(12) United States Patent
Fehr et al.

(10) Patent No.: US 7,322,956 B2
(45) Date of Patent: Jan. 29, 2008

(54) SYSTEM AND METHOD FOR MIXING AT LEAST FOUR COMPONENTS

(75) Inventors: Daniel Fehr, Zurich (CH); Astrid Neidhardt, Zurich (CH); Christian Damm, Sissach (CH)

(73) Assignee: Straumann Holding, AB, Basel (CH)

( * ) Notice: Subject to any disclaimer, the term of this patent is extended or adjusted under 35 U.S.C. 154(b) by 0 days.

(21) Appl. No.: 10/890,149

(22) Filed: Jul. 14, 2004

(65) Prior Publication Data

US 2005/0027240 A1    Feb. 3, 2005

(30) Foreign Application Priority Data

Jul. 15, 2003   (EP)   .................. 03405537

(51) Int. Cl.
*A61M 37/00*   (2006.01)

(52) U.S. Cl. .................. 604/82; 604/110; 604/84; 604/56; 604/416

(58) Field of Classification Search .................. 604/81, 604/82, 83, 84, 86, 191
See application file for complete search history.

(56) References Cited

U.S. PATENT DOCUMENTS

| | | | |
|---|---|---|---|
| 3,767,085 A * | 10/1973 | Cannon et al. ............... 222/82 |
| 4,735,616 A | 4/1988 | Eibl et al. .................... 604/191 |
| 4,743,229 A | 5/1988 | Chu ............................ 604/82 |
| 4,994,029 A | 2/1991 | Rohrbough ................... 604/88 |
| 5,116,315 A | 5/1992 | Capozzi et al. ............... 604/82 |
| 5,520,658 A * | 5/1996 | Holm ......................... 604/191 |
| 6,234,196 B1 | 5/2001 | Fischer et al. ........... 137/493.8 |
| 6,328,229 B1 | 12/2001 | Duronio et al. ............. 239/399 |
| 6,454,739 B1 * | 9/2002 | Chang .......................... 604/82 |
| 6,458,095 B1 * | 10/2002 | Wirt et al. .................... 604/82 |
| 6,475,183 B1 | 11/2002 | Epstein et al. ................ 604/82 |
| 2001/0037091 A1 | 11/2001 | Wironen et al. ............ 604/236 |
| 2002/0198490 A1 | 12/2002 | Wirt et al. .................... 604/82 |
| 2003/0055384 A1 * | 3/2003 | Enrenfels et al. ........... 604/191 |

FOREIGN PATENT DOCUMENTS

| | | |
|---|---|---|
| DE | 19636622 | 3/1998 |
| EP | 0292472 B1 | 5/1988 |
| EP | 0292472 B1 * | 5/1988 |
| EP | 0 292 472 B1 | 5/1998 |
| FR | 2412475 | 7/1979 |

* cited by examiner

*Primary Examiner*—Kevin C. Sirmons
*Assistant Examiner*—Phillip Gray
(74) *Attorney, Agent, or Firm*—Rissman Jobse Hendricks & Oliverio, LLP

(57) ABSTRACT

System for mixing four components including a first syringe arrangement and a second syringe arrangement each with two chambers for holding components. Each of the two respective chambers of the syringe arrangements are connected in a uniquely defined fashion due to specific means for connecting the syringe arrangements. A component held by one chamber is mixed with a component of the corresponding other chamber by transfer into the other chamber. After mixing and disconnecting the second syringe arrangement from the first syringe arrangement, the two component mixtures in the chambers of the first syringe arrangement are further mixed and discharged by means of a mixing device which is to be connected to the first syringe arrangement. The connecting means allows connecting of the mixing device to the first syringe arrangement only after removal of the second syringe arrangement and a portion of the connecting means.

7 Claims, 15 Drawing Sheets

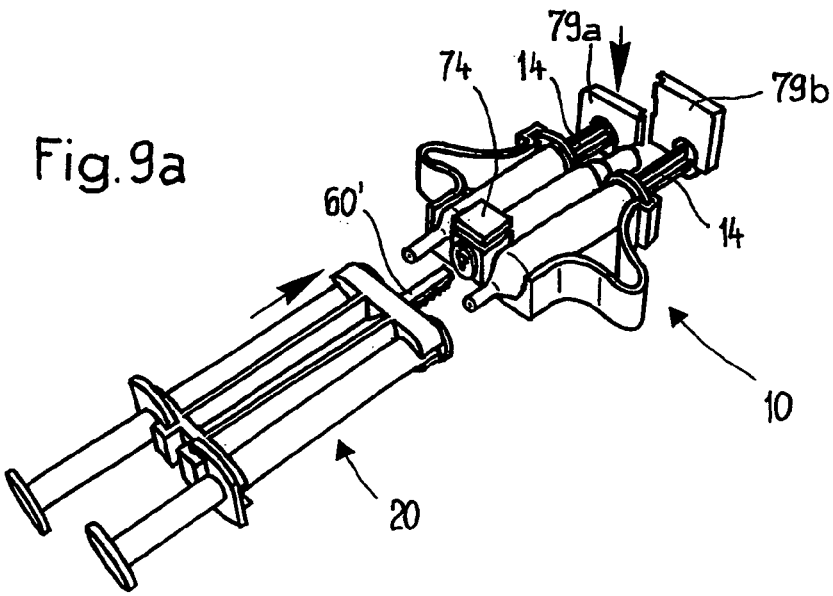
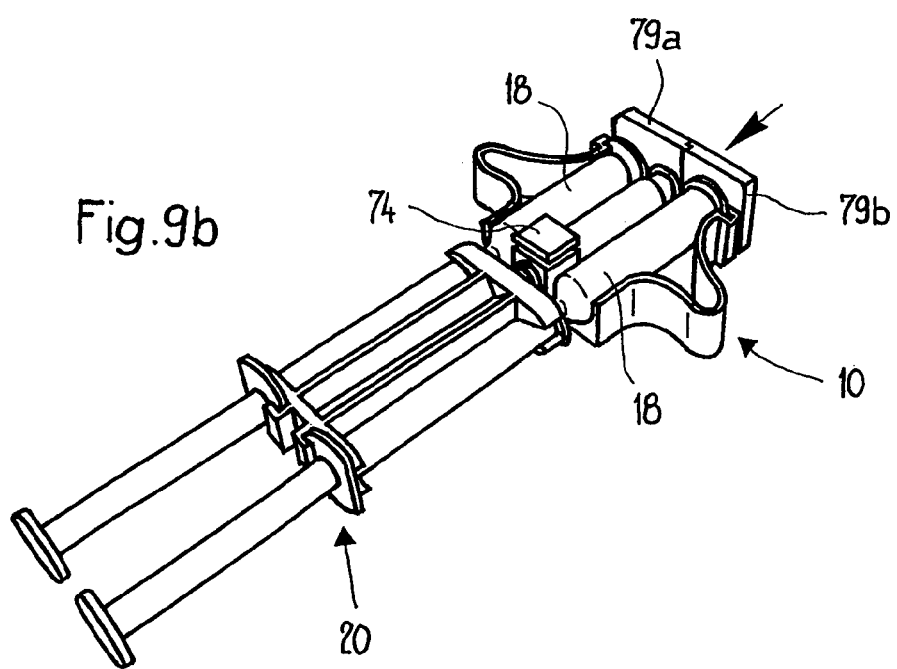

SYSTEM AND METHOD FOR MIXING AT LEAST FOUR COMPONENTS

RELATED APPLICATIONS

This application claims a benefit of priority under 35 U.S.C. § 119 to European Patent Application 03 405 537.6, filed Jul. 15, 2003.

FIELD OF THE INVENTION

The invention relates to a system and a method for mixing at least four components having the features of the preamble of the independent patent claims.

BACKGROUND OF THE INVENTION

In many applications, in particular in the field of medicine, it is necessary to mix various components with one another shortly before application. These may be in particular components of a two-component compound which harden on contact with one another, for example teeth filling compounds.

Such components are frequently packaged in disposable syringes, for example for hygienic reasons. U.S. Pat. Nos. 5,116,315, 4,735,616, 6,328,229 or US 2002/0042591 disclose, for example, mixing arrangements in which the components which are contained in two syringes are discharged together through a mixer and mixed in the process.

Furthermore it is known to connect two syringes to one another at their ends so that the components which are contained in the syringes can be thoroughly mixed by backward and forward transfer. Such arrangements are known, for example, from U.S. Pat. Nos. 4,743,229, 4,994,029, 6,234,196 or US 2002/0055708.

A disadvantage of these known arrangements is that it is completely impossible to mix more than two components with one another, or they can be mixed with one another only with increased effort. In particular in the case of biomedical applications, it is however frequently desirable firstly to mix two components, for example two polymers, with buffers and then to bring them in contact with one another in order to crosslink them or polymerize them. The polymers and aqueous solutions are frequently stored separately from one another in this context for reasons of stability.

SUMMARY OF THE INVENTION

According to one embodiment of the invention a system and a method are provided for mixing at least four components which permits the components to be mixed easily. In select embodiments, this system is intended to be capable of being manufactured easily and cost-effectively. In addition, in select embodiments, it is possible to process the components hygienically, in particular to mix them without contamination.

The system according to the invention is used for mixing at least four components. The invention will be explained with reference to four components both here and below. The same system could however basically also be used for mixing more, for example 6 components. The system has a first and second syringe arrangement. The first and second syringe arrangements each contain at least two chambers for receiving one component each. Each of the four components is therefore contained in one of two chambers of one of the two syringe arrangements. Each chamber of one of the syringe arrangements is connected in a detachable fashion to a chamber of the other syringe arrangement so that each component which is contained in a chamber of one of the syringe arrangements can be transferred into a chamber of the other syringe arrangement and can be mixed with the component contained in this chamber. By means of this system it is possible, in a first step, to mix in each case two components with in each case two other components by transferring from one of the syringe arrangements into the other syringe arrangement so that two first mixtures are formed. After the transfer, these first mixtures are contained in the chambers of one syringe arrangement. These first mixtures can then be discharged from this syringe arrangement and mixed with one another so that a second mixture composed of all four components is produced.

According to one preferred embodiment, the system therefore also has a mixing arrangement. The mixing arrangement is typically a static mixer. The mixing arrangement can be connected to the chambers of one of the syringe arrangements so that the mixtures which are contained in the chambers can be mixed further with one another by being discharged from the chambers and through the mixing arrangement. By means of such a system it is possible firstly to mix in each case two components with one another in two steps. By connecting one of the syringe arrangements in which the mixtures are contained to a mixing arrangement, these mixtures can subsequently be mixed in a further step to form the desired mixture. The handling is very easy because the syringe arrangements which are used as containers for the components are used twice for mixing.

In order to prevent the first and second syringe arrangements being inadvertently incorrectly combined, in one preferred embodiment the system can also have means which ensure that the connection of the syringe arrangements to one another is uniquely defined, that is to say only a single connection is possible. It is conceivable, for example, to use a coding sleeve on one of the syringe arrangements in which a projection on the other syringe arrangement can be inserted into precisely only one position.

According to a further preferred embodiment, at least one of the syringe arrangements also has syringe plungers which can be connected to one another. The plungers can typically be plugged or clipped together. Such a connection ensures that the components which are contained in the two chambers it are expelled uniformly. As a result of the uniform expulsion of the components in the two chambers, uniform mixing during the transfer into the other chambers of the other syringe arrangement and/or during the discharging of the first mixtures through the mixing arrangement is also brought about.

The syringes of one of the syringe arrangements are particularly preferably composed of glass, while the syringes of the other syringe arrangement are particularly preferably composed of plastic. Polymers such as, for example, PEG acrylates, PEG thiol for forming hydrogels and for use as diaphragms, which prevent the growth of a mesh at the place of application, are typically located in the chambers of the syringe arrangements which are formed from glass. In the syringes which are formed from plastic there are typically liquids, such as, for example, aqueous carboxy-methyl cellulose solution (CMC solution) with or without buffer salts, if appropriate with catalysts. In particular basic buffers are preferred when buffers are used in these fluids.

The syringes are preferably embodied as conventional syringes which, when inserted into a holder, can be combined to form the described syringe arrangements.

The connecting arrangement between the first and second syringe arrangements is also preferably constructed in such a way that the connection can be detached only if the mixed components are located in the chambers of one of the syringe arrangements. This ensures that the syringe arrangements cannot be separated from one another again until after the components have been correctly transferred from one syringe arrangement into the other syringe arrangement. Therefore, the mixing arrangement cannot be fitted on until the mixtures are located in the desired syringe arrangement. For this purpose it is possible, for example, to provide a latching arrangement which can be released only when the plungers of the syringes are pushed back.

The detachable connection between the syringe arrangements is preferably embodied as a snap-action connection. In this way, the two syringe arrangements can be connected to one another easily and in a clearly defined end position. However, other connecting mechanisms are of course also conceivable. The mixing arrangement can preferably also be connected to one of the syringe arrangements by means of a snap-action connection. It is conceivable, but not absolutely necessary, to use the same connecting means for the connection between the syringe arrangements on the one hand and for the connection between one of the syringe arrangements and the mixing arrangement, on the other.

In order to monitor the mixing process during the discharging of the mixtures through the mixing arrangement, it is also conceivable to make the mixing arrangement of at least partially transparent design. The mixing process can be monitored here through a type of viewing window.

According to a further preferred embodiment, the mixing arrangement can also have a bent tip. This makes it easier to apply it in areas which are difficult to access, for example in the mouth area.

The holder according to the invention is used for holding at least two syringes and is designed to connect to a second holder.

The method according to the invention is used for mixing at least four components. In the method, components are firstly prepared in each case in at least two chambers of two syringe arrangements. These chambers are each provided with discharge openings. The discharge openings of in each case one chamber of one of the syringe arrangements are then connected to, in each case, one chamber of the other syringe arrangement. Then, the components from the chambers of the first syringe arrangement are transferred in each case into one chamber of the second syringe arrangement. The transfer is typically carried out by expelling the components by means of a plunger of the syringe. When the transfer takes place, the transferred components are mixed with the components which are contained in the second syringe arrangement. In the process, first mixtures are formed. In a last step, the first mixtures which are contained in the chambers are discharged and mixed, accompanied by further mixing with one another, to form a second mixture.

According to a preferred exemplary embodiment of the method according to the invention, the components which are mixed by means of an initial transfer are transferred back from the chambers of the second syringe arrangement into the chambers of the first syringe arrangement for the purpose of further mixing.

According to a further preferred exemplary embodiment, the first mixtures which are formed in this way are discharged through a static mixer and in the process mixed to form the second mixtures.

BRIEF DESCRIPTION OF THE DRAWINGS

The invention is explained in more detail below with reference to the drawings and in exemplary embodiments. In said drawings:

FIG. 19 is a likewise perspective illustration of the first syringe arrangement with a mixing device fitted on.

DETAILED DESCRIPTION

Figure 1:
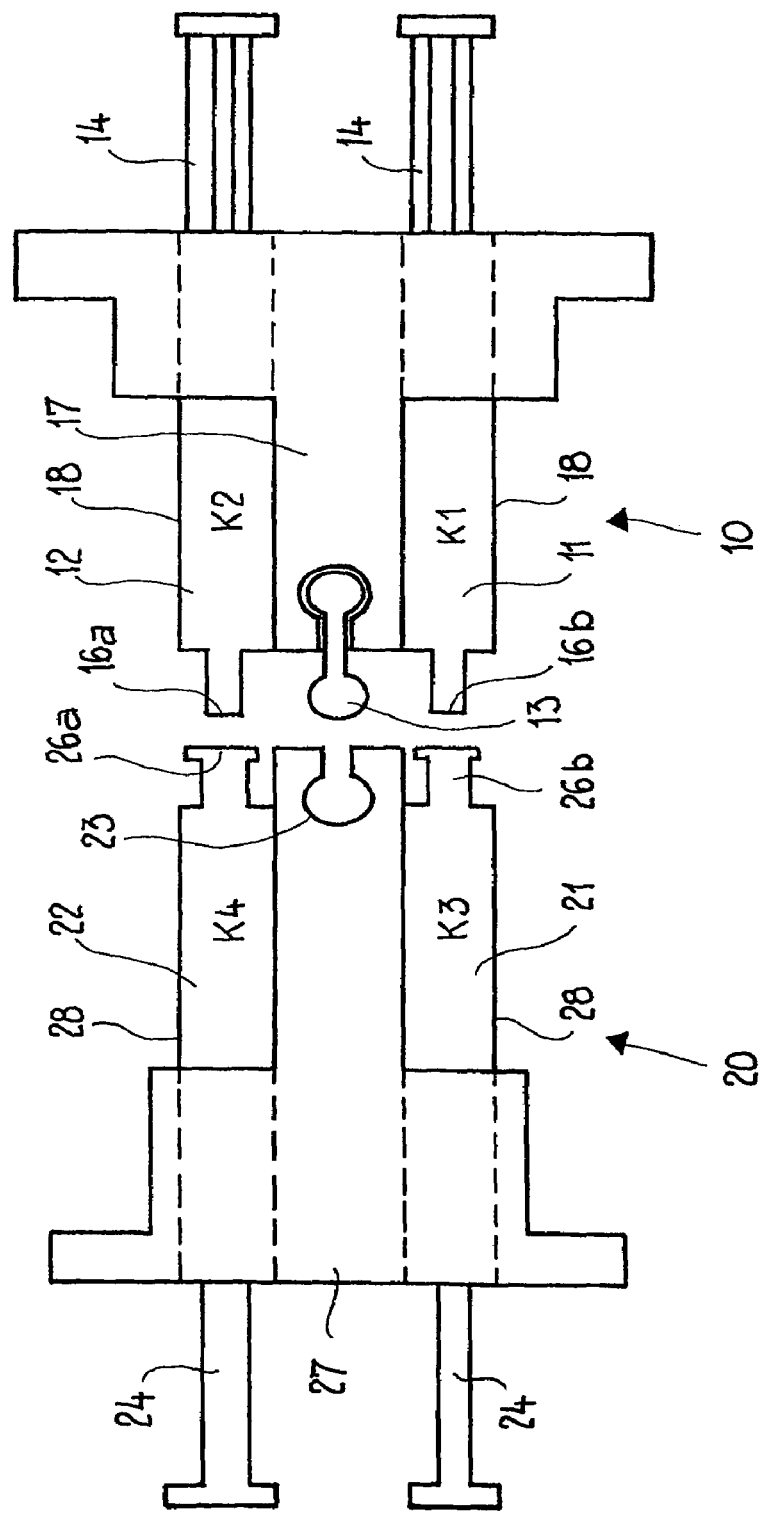
FIG. 1 is a schematic illustration of an exemplary embodiment of two syringe arrangements according to the invention.

FIG. 1 shows, in a schematic view, a first syringe arrangement 10 and a second syringe arrangement 20. The first syringe arrangement 20 has two syringes 18 which are inserted into a holder 17 and as a result connected to one another. The two syringes 18 each have a chamber 11, 12. The chambers 11, 12 contain components K1, K2.

The second syringe arrangement 20 also has two syringes 28 which are connected to one another via a holder 27. The syringes 28 have chambers 21, 22 for holding components K3 and K4.

The syringes 18 and 28 are constructed in a fashion known per se and have plungers 14 and 24 for discharging the components K1, K2, K3, K4 contained in the syringes, through discharge openings 16a, 16b or discharge openings 26a, 26b. The syringes 18 of the first syringe arrangement 10 can typically be glass syringes without a Luer lock from the manufacturer Becton Dickinson. The syringes 28 of the second syringe arrangement 20 are typically plastic syringes with a male inlet from Ultradent.

Figure 2:
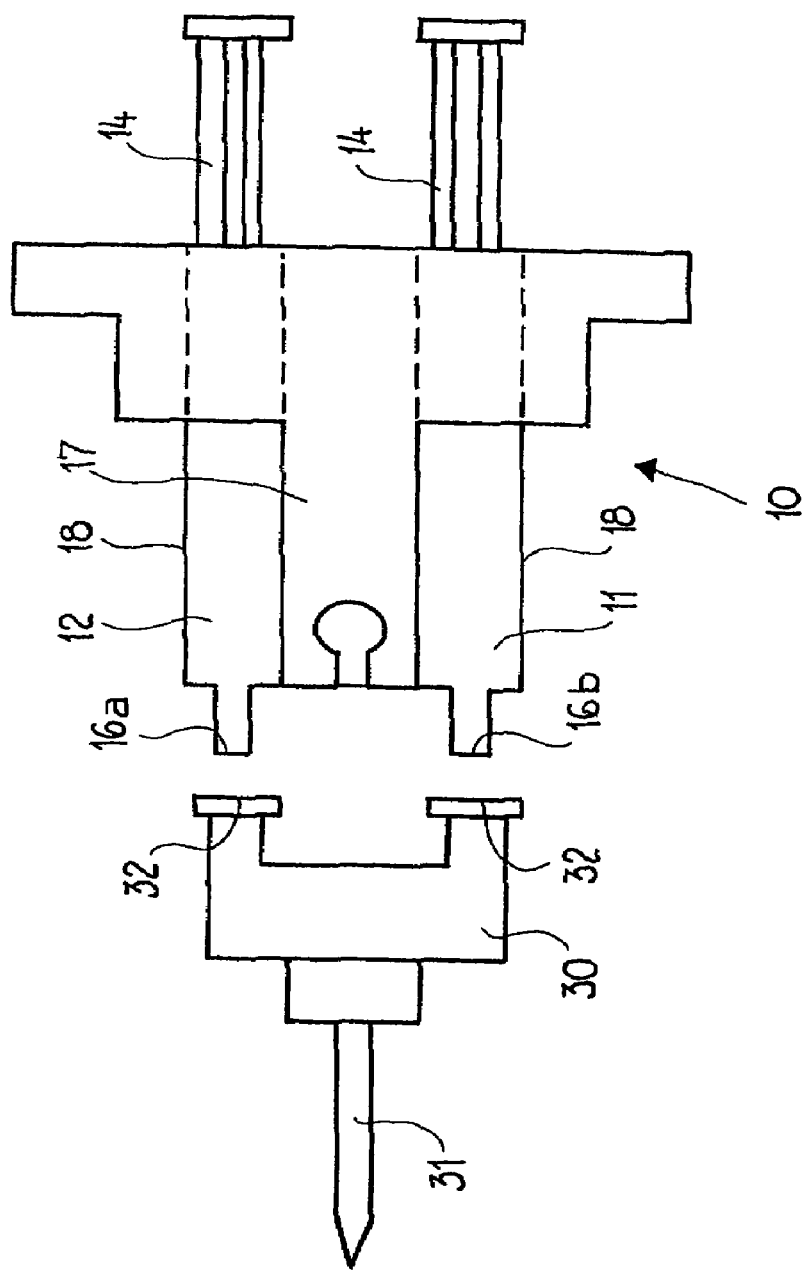
FIG. 2 is a schematic illustration of a static mixer according to the invention, FIGS. 3a, b, c are schematic illustrations of the method according to the invention for mixing components.

The first syringe arrangement 10 has a cam 13 which can be clipped into a recess 23 on the second syringe arrangement 20. The first syringe arrangement 10 and the second syringe arrangement 20 can be connected to one another by means of the recess 23 and the cam 13 in such a way that the discharge openings 16a, 26a and 16b, 26b of the syringes 18, 28 can each be connected to one another.

the system according to the invention also has a mixing device 30. The mixing device 30 which is embodied as a static mixer is illustrated schematically in FIG. 2. The mixing device 30 has two openings 32 which can be connected to the discharge openings 16a, 16b of the first syringe arrangement 10. The mixing device 30 is also provided with a tip 30 by means of which components which are mixed in the mixing device 30 can be discharged.

Figure 3A:
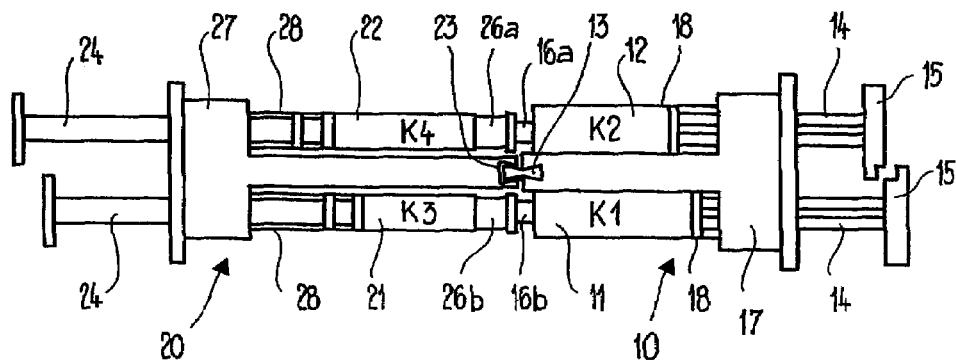
Figure 3B:
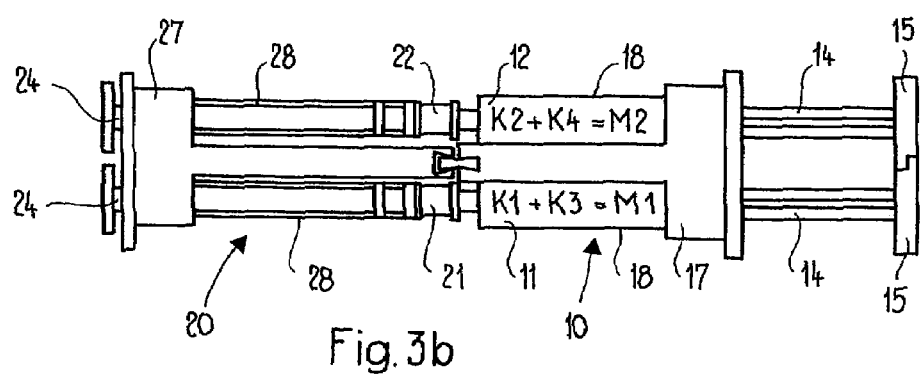
Figure 3C:
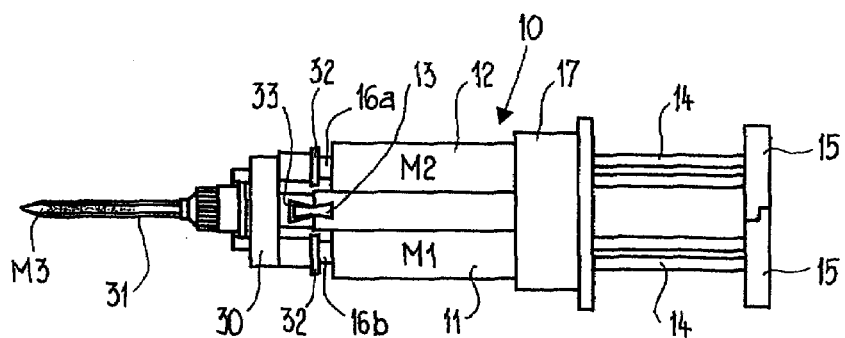

The mixing process with the mixing device 30 according to the invention is shown schematically in FIGS. 3a to 3c.

With the system and method according to the invention it is to be possible to mix four components K1, K2, K3 and K4 with one another. The components are typically a buffer such as, for example CMC with water or various basic buffers and PEG acrylates or PEG thiol.

The components are each contained in syringes 18 and 28. Two syringes 18 and 28 are connected to a holder 17 or 27 to form a first syringe arrangement 10 or to form a second syringe arrangement 20. This connection may already be part of the mixing process. However, it is also conceivable to make the syringe arrangements 10, 20 available in a premounted form with two syringes each.

The holders 17, 27 are constructed in such a way that the caps (which are not shown) of the syringes, in particular the plastic syringes 28, can be moved by simply turning them. In particular, the intention is that the holder 27 does not impede this rotary movement.

In a first step of the mixing process, the syringe arrangements 10, 20 are connected to one another in a seal-forming fashion by their discharge openings 16a, 16b and 26a, 26b. For this purpose, a holding device is used with a cam 13 and recess 23 by means of which the two holders 17, 27 of the syringe arrangements 10, 20 can be connected to one another in a clippable fashion.

In order to mix the components, the components K1, K2 are firstly transferred from the chambers 11, 12 of the first syringe arrangement into the chambers 21, 22 of the second syringe arrangement. This is carried out by activating the plungers 14 of the first syringe arrangement 10 so that the components K1, K2 are forced through the discharge openings 16b, 16a into the chambers 21, 22 of the second syringe arrangement 20. During this process, the components K1, K2 are each mixed with the components K3, K4 which are already contained in the chambers 21, 22 of the second syringe arrangement 20. After this transfer step, the chambers 11, 12 of the first syringe arrangement 10 are empty, and mixtures M1, M2 composed of the components K1 and K3 or of the components K2 and K4 are located in the chambers 21, 22 of the second syringe arrangement 20. This situation is not illustrated in FIGS. 3a to 3c. In order to improve further the thorough mixing of the mixtures M1 and M2, these mixtures are then transferred back from the second syringe arrangement 20 into the first syringe arrangement 10.

FIG. 3b shows the mixtures M1 and M2 which have been transferred back. The chambers 21, 22 of the second syringe arrangement 20 are empty. In this situation it is possible to disconnect the first syringe arrangement 10 again from the second syringe arrangement 20. (See description relating to FIG. 5b.) Instead of the second syringe arrangement 20, in a subsequent step (see FIG. 3c) a mixing device 30 is connected to the discharge openings 16a, 16b of the first syringe arrangement 10. For this purpose, the mixing device 30 has openings 32 which fit the discharge openings 16a, 16b in a seal-forming fashion. In addition, the mixing device 30 has a snap-action device 33 which can be detachably connected with a snap action to the cam 13 of the first syringe arrangement 10, which forms a projection. By pressing the plungers 14 of the first syringe arrangement 10, the mixtures M1, M2 which are contained in the chambers 11, 12 are transferred through the mixing device 13 and in the process mixed together to form a mixture M3 which can be discharged through the tip 31 of the mixing device 30.

The mixing device 30 is of conventional design.

In order to ensure that the discharging of the components takes place uniformly during the respective transfer, the first syringe arrangement 10 is provided with a connecting device 15. The plungers can be connected to one another by means of two clips which are fitted onto the plungers 14. As a result, the mixtures M1, M2 can be expelled uniformly through the mixing device 30, but also a uniform transfer of the components K1, K2 (see FIG. 3a) into the chambers 21, 22 of the second syringe arrangement is also already ensured.

Figure 4:
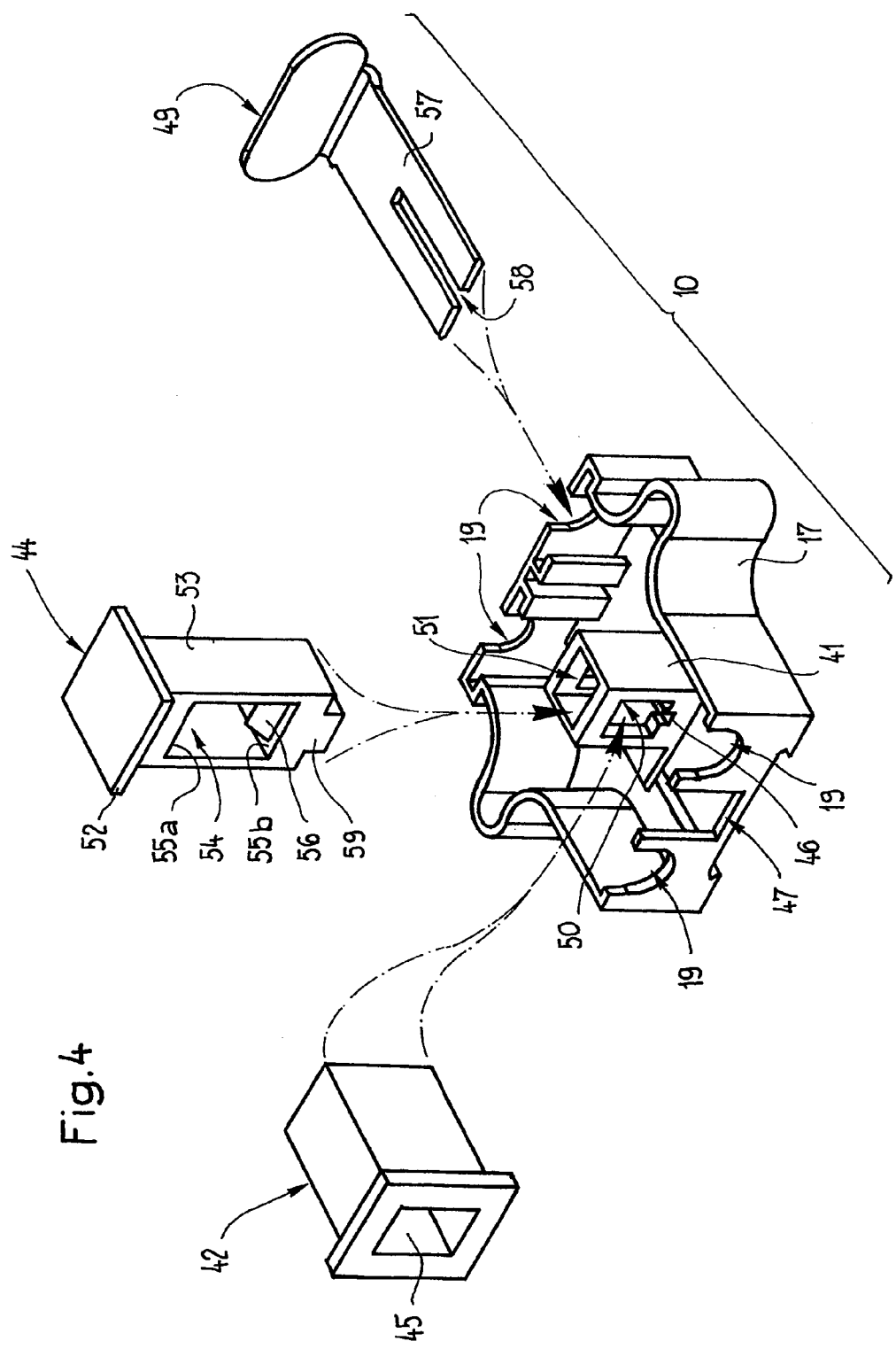
FIG. 4 is an exploded illustration of the connecting mechanism of a first syringe arrangement of a first exemplary embodiment.

FIG. 4 shows, in a schematic exploded illustration, an embodiment of a first syringe arrangement 10 with a connecting mechanism which prevents the two syringe arrangements 10, 20 from becoming detached before mixing takes place. In a way similar to the preceding FIGS. 2 and 3, syringes 18 are inserted into the syringe receptacles 19 of the holder 17. The holder 17 is also provided on the end side between the syringe receptacles 19 with an insertion opening 47 for feeding through a connecting element (see following FIGS. 5a to 5c). The holder 17 has a mounting element 41 for holding an unlocking knob 44 by means of which the first and second syringe arrangements 10, 20 can be disconnected from one another again after mixing has taken place. The unlocking knob 44 is displaceably inserted into the longitudinal opening 51 of the mounting element 41. The mounting element 41 also has an opening 50 with a rectangular cross section. A coding sleeve 42 is inserted into the opening 50. At the lower edge of the opening 50, a recess 46 is formed which provides a guide for the connecting projection 34 of the mixing device 30 (FIGS. 5c, 6d). The opening 50 and longitudinal opening 51 run perpendicularly with respect to one another.

The coding sleeve 42 contains an opening 45 for the insertion of a connecting projection 60 (not shown) of the second syringe arrangement 20. There is a latching clip 43 (not shown in FIG. 4) which is arranged on the inner, upper boundary face of the opening 45 of the coding sleeve 42 and moves into engagement with the saw teeth of the connecting projection 60 (see FIG. 5a).

The unlocking knob 44 has a head part 52 and a body part 53. A depression 54 for holding the coding sleeve 42 is provided in the body part 53. The depression 54 is defined by an upper boundary face 55a and a lower boundary face 55b. A latching cam 56, which holds back a latching cam of the coding sleeve 42, is arranged on the lower boundary face 55b.

The plungers 14 of two syringes which are inserted in the holder 17 are connected to one another by means of a connecting plate 49. The connecting plate 49 has an extension 57 as well as a groove 58. The groove 58 is constructed in such a way that it is in positive locking engagement with the projection 59 of the unlocking knob 44.

The function of the coding sleeve will now be described more precisely with reference to FIGS. 5a, 5b and 5c.

The second syringe arrangement 20 has the connecting projection 60. FIG. 5a shows only the connecting projection 60, which is connected at 20 in a suitable way (see for example FIGS. 6a to 6c) to the second syringe arrangement. The connecting projection 60 of the second syringe arrangement 20 can be inserted into the opening 45—with a preferably rectangular cross section—in the coding sleeve 42. On its other side 61, the connecting projection 60 has saw teeth 62. By means of the saw teeth 62, the connecting projection 60 can be latched to the sprung latching clip 43 on the upper wall of the opening 45 of the coding sleeve 42. Once the connecting projection 60 has been plugged into the coding sleeve 42, the projection 60 can no longer easily be removed from the coding sleeve 42 by reason of the latching of the latching clip 43 to the saw teeth 62.

The unlocking knob 44 can be displaced by a distance Δl in the direction of the longitudinal opening 51. In FIG. 5a, the unlocking knob 44 is shown in an upper position in which the coding sleeve 42 is held in the mounting element 41 by reason of the interaction between the latching cam 48 of the coding sleeve 42 and the latching cam 56. As a result of the unlocking knob 44 being pressed down in the direction of the arrow D, the latching cam 56 on the unlocking knob 44 disengages from the latching cam 48 of the coding sleeve 42. As a result, the coding sleeve 42, and thus also the connecting projection 60 which is latched into the coding sleeve 42, can be removed from the mounting element 41.

Figure 5A:
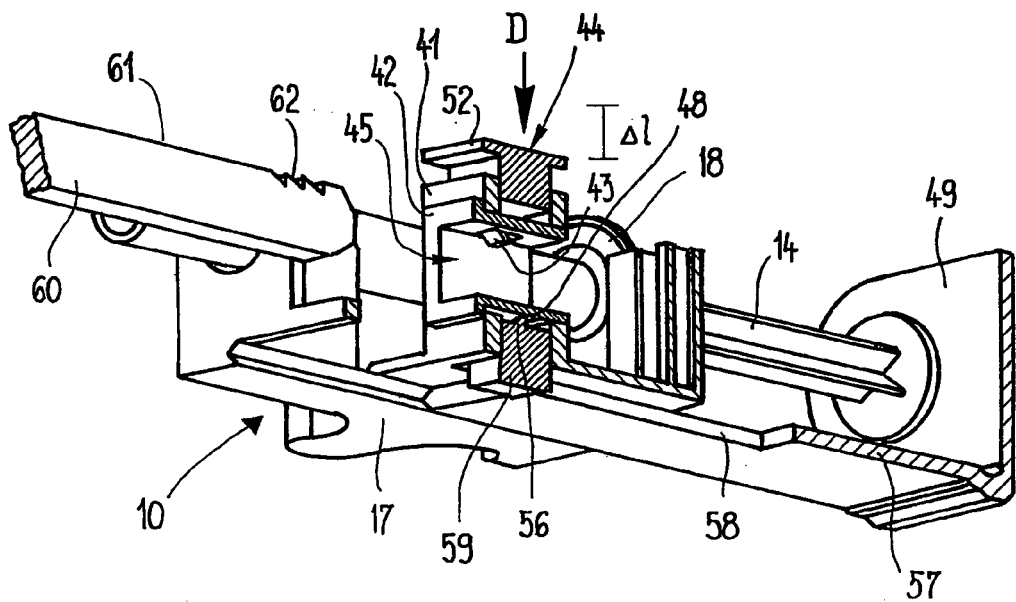
FIGS. 5a to 5c are detailed three-dimensional illustrations of a first syringe arrangement in a first embodiment, the locking and unlocking of a second syringe arrangement are illustrated as a section parallel to the axis of movement of the connecting projection.
Figure 5B:
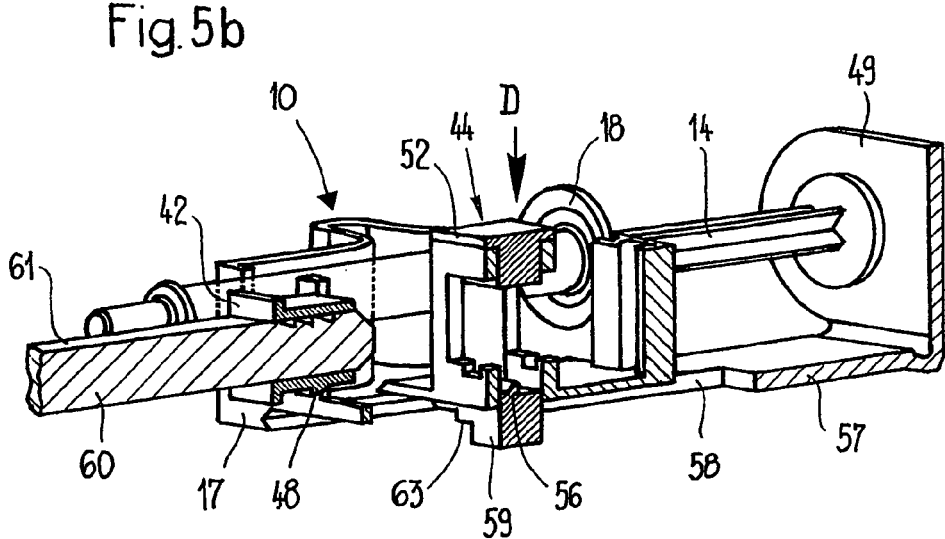
Figure 5C:
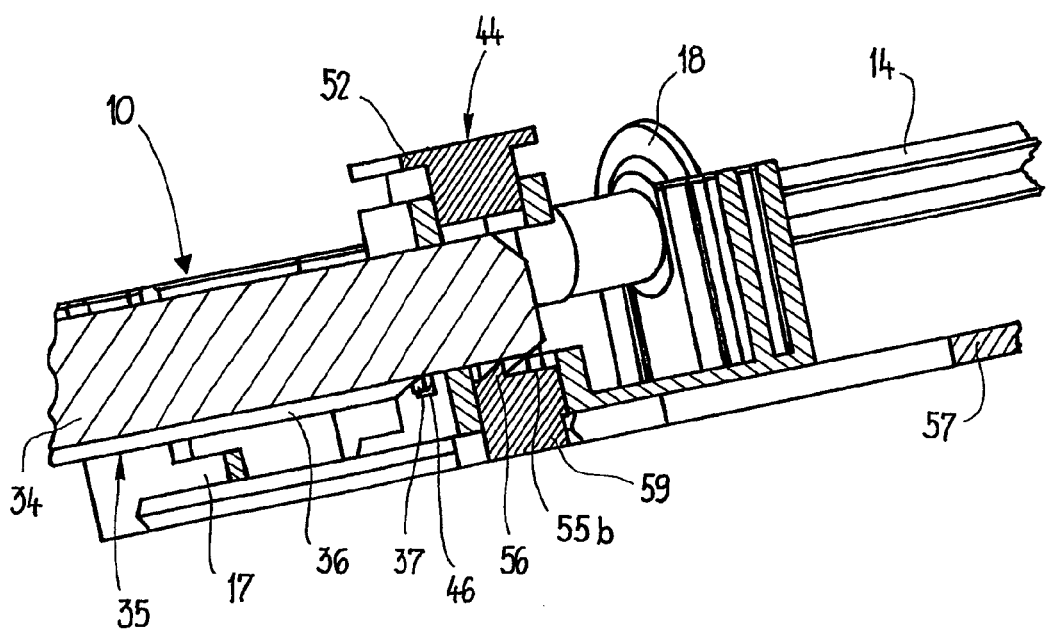
Figure 6A:
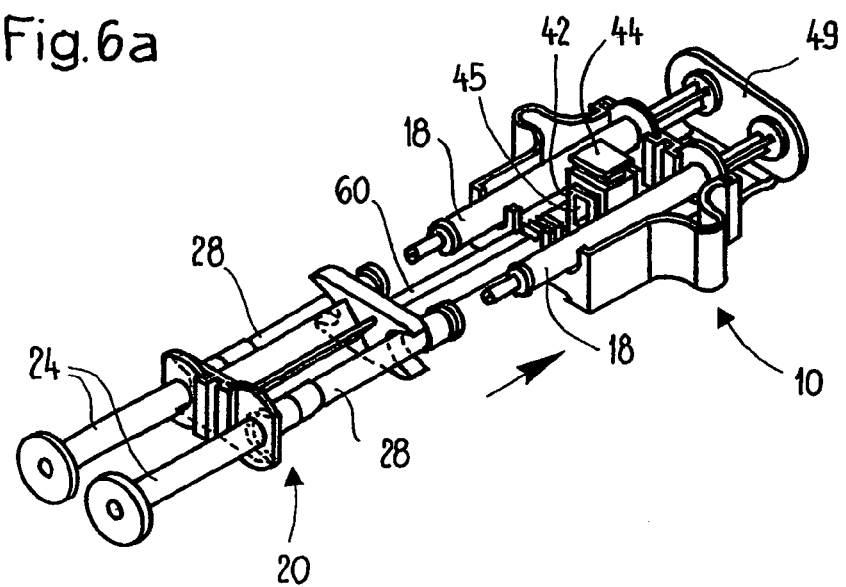
FIGS. 6a to 6d are schematic illustrations of the mixing process of the embodiment according to FIGS. 5a to 5c in a three-dimensional form.

FIGS. 5a and 5b also show the arrangement which ensures that the locking knob 44 can be pressed downwards only in the direction of the arrow D if the plungers 14 of the syringes 18 are in the opened position. This ensures that the first and second syringe arrangements 10, 20 can be separated from one another only if the plungers 14 of the first syringe arrangement 10 are in the opened position, that is to say only if the fluid which is mixed as a result of the backward and forward transfer is located in the syringes 18 of the first syringe arrangement 10.

FIG. 5a shows that the connecting plate 49, which connects the plungers 14 to one another, has the extension 57 which is arranged in a displaceable fashion on the underside of the holder 17. The extension 57 has the groove 58. The projection 59 which is arranged on the underside of the unlocking knob 44 is guided in the groove 58 (see FIG. 5a). If the plungers 14 are pressed into the syringes 18, the projection 59 of the unlocking knob 44 lies in the groove 58 of the extension 57. The underside 63 of the locking knob 44 lies here on the upper side of the extension 57. As a result, the locking knob 40 can no longer be pressed downwards in the direction of the arrow D. If the pistons 14 are in the opened position (see FIG. 5b), the underside 63 of the unlocking knob 44 is cleared. The unlocking knob 44 can then be pressed in the direction of the arrow D, and the coding sleeve 42 can be removed with the connecting projection 60 inserted in it.

FIG. 5c shows the latching of the connecting projection 34 of the mixing device 30 in the unlocking knob 44. The connecting projection 34 of the mixer 30 has a profiling 36 on its underside 35. The profiling 36 is selected in terms of its shape in such a way that it fits into the recess 46 of the mounting element 41 or into a depression 54 in the body part 53 of the unlocking knob 44. On the underside 35 of the connecting projection 34, saw teeth 37 are provided which latch with the latching cam 56 of the unlocking knob 44. As a result, after the connection to the first syringe arrangement 10, the mixer 30 can be released only by pressing the unlocking knob 44.

Figure 6B:
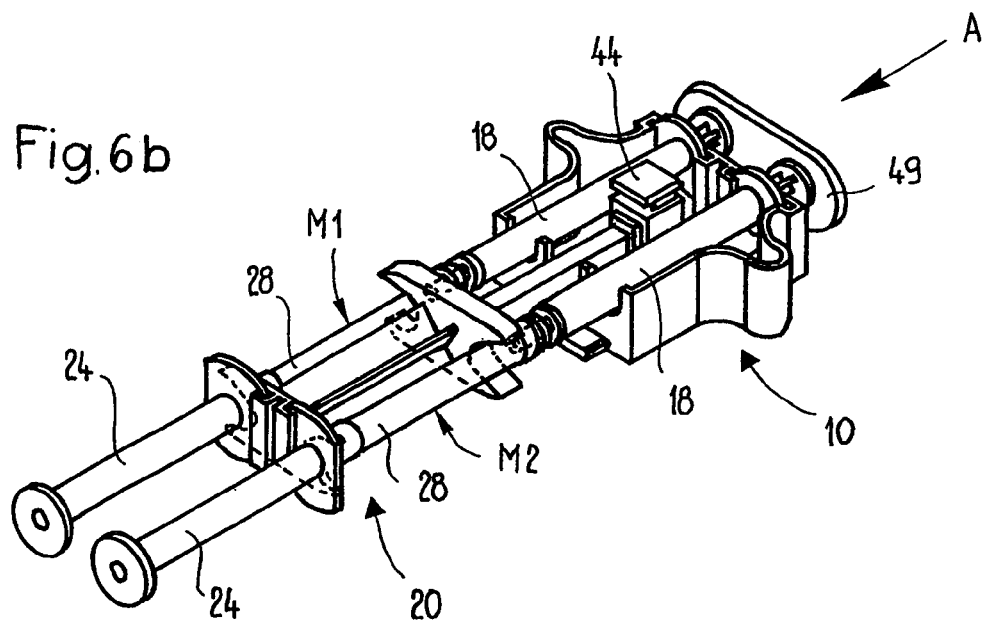
Figure 6C:
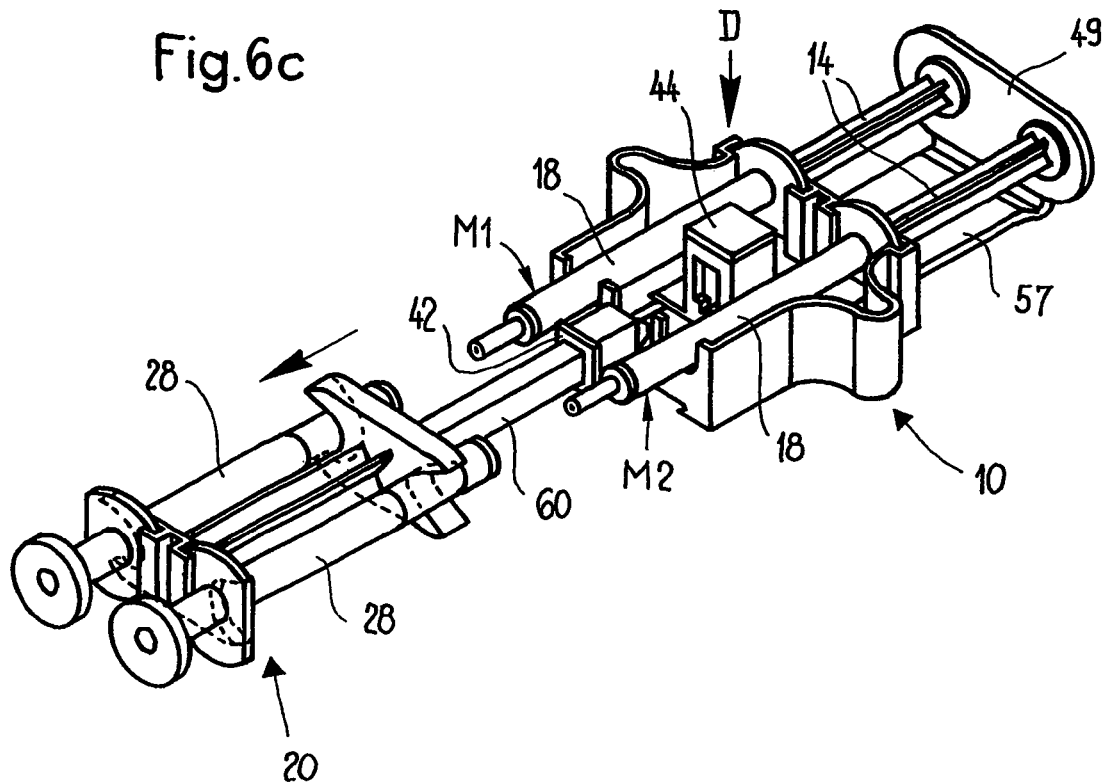
Figure 6D:
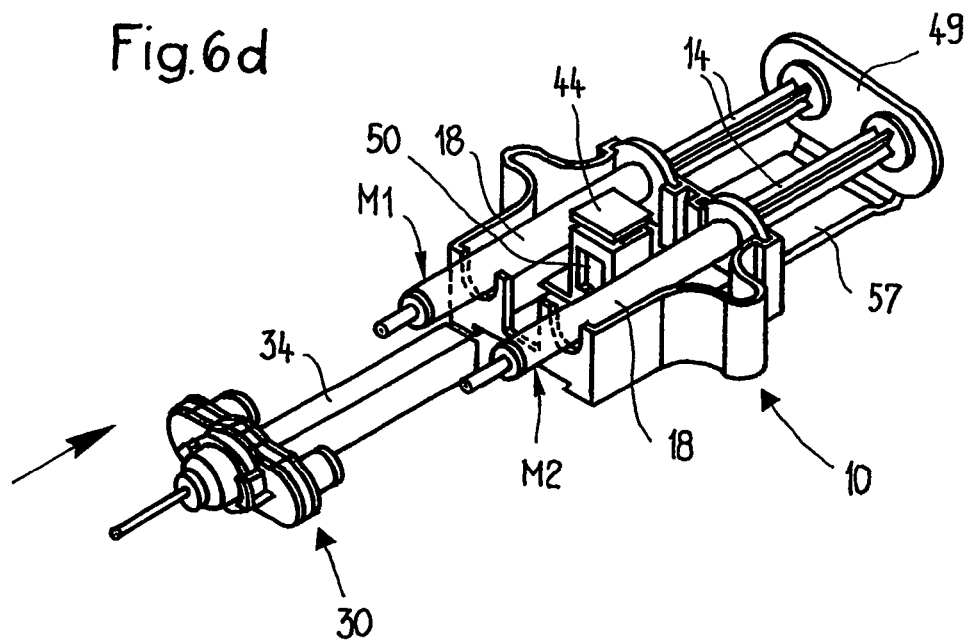

The mixing process is shown below in FIGS. 6a to 6d. Before the mixing, the components which are to be mixed are contained in the syringes 28 of the second syringe arrangement 20 or in the syringes 18 of the first syringe arrangement 10. For the purpose of mixing, the two syringe arrangements 10, 20 are connected to one another. For this purpose, the extension projection 60 is inserted into the opening 45 of the coding sleeve 42 of the first syringe arrangement 10. Optionally, it is possible, by selecting the cross section of the extension projection 60 and the opening 45 in the coding sleeve 42, to ensure that the two syringe arrangements 10, 20 can be combined only in a precisely defined fashion. The combined syringe arrangements 10, 20 are shown in FIG. 6b.

In order to mix the components, the connecting plate 49 of the first syringe arrangement 10 is pressed in the direction of the arrow A. As a result, the components K1, K2 which are contained in the syringes 18 are transferred into the syringes 28 of the second syringe arrangement 20. As a result, the plungers 24 of the second syringe arrangement 20 are pressed into the opened position (see FIG. 6b). In this position, the syringe arrangements 10, 20 can no longer be separated from one another, since the extension projection 60 is firmly latched into the coding sleeve 42 and the unlocking knob 44 cannot be moved downwards in order to clear the coding sleeve 42 (see also FIG. 5a).

In a further step (between FIG. 6b and FIG. 6c), the plungers 24 of the second syringe arrangement are activated. In the process, the mixtures M1, M2 which are contained in the syringes 28 of the second syringe arrangement are mixed further and transferred back into the syringes 18 of the first syringe arrangement 10. The plungers 14 in the first syringe arrangement 10 are pressed into the opened position. At the same time, the connecting plate 49, and thus also the extension 47, are displaced. In this way, the locking knob 44 is cleared (see FIG. 5b) so that it can then be pushed downwards in the direction of the arrow D. As a result, the coding sleeve 42 is cleared and the second syringe arrangement 20 can be removed with the coding sleeve 42 which remains on the connecting projection 60.

In order to terminate the mixing process, the mixing device 30 is fitted onto the first syringe arrangement 10 (see FIG. 6d). The mixing device 30 also has a connecting projection 34 (see also FIG. 5c). The shape of the profiled connecting projection 34 of the mixing device 30 is selected such that it fits into the opening 50 (with the recess 46) of the mounting element 41 and the depression 54 of the body part 53 of the unlocking knob 44, respectively. As illustrated in FIG. 5c, saw teeth 37, which latch with the latching cam 56 of the unlocking knob 44, are provided on the underside 35 of the connecting projection 34. As a result, after connection to the first syringe arrangement 10, the mixer 30 can be detached only by pressing the unlocking knob 44. In order to mix the mixtures M1, M2 in the syringes 18 of the first syringe arrangement 10, the connecting plate 49 is in turn pressed. As a result, the plungers 14 are activated and the mixtures M1, M2 are discharged through the mixing device 30. After the discharging, the mixing device 30 remains firmly connected to the first syringe arrangement 10 by means of the connecting projection 34. As a rule, the mixing device 30 remains at the first syringe arrangement 10 after the discharging of the mixtures. However, the mixing device 30 can nevertheless be exchanged for a replacement if there are faults such as, for example, blockage or premature hardening of the mixture from M1 and M2 in the mixing device 30.

Figure 7:
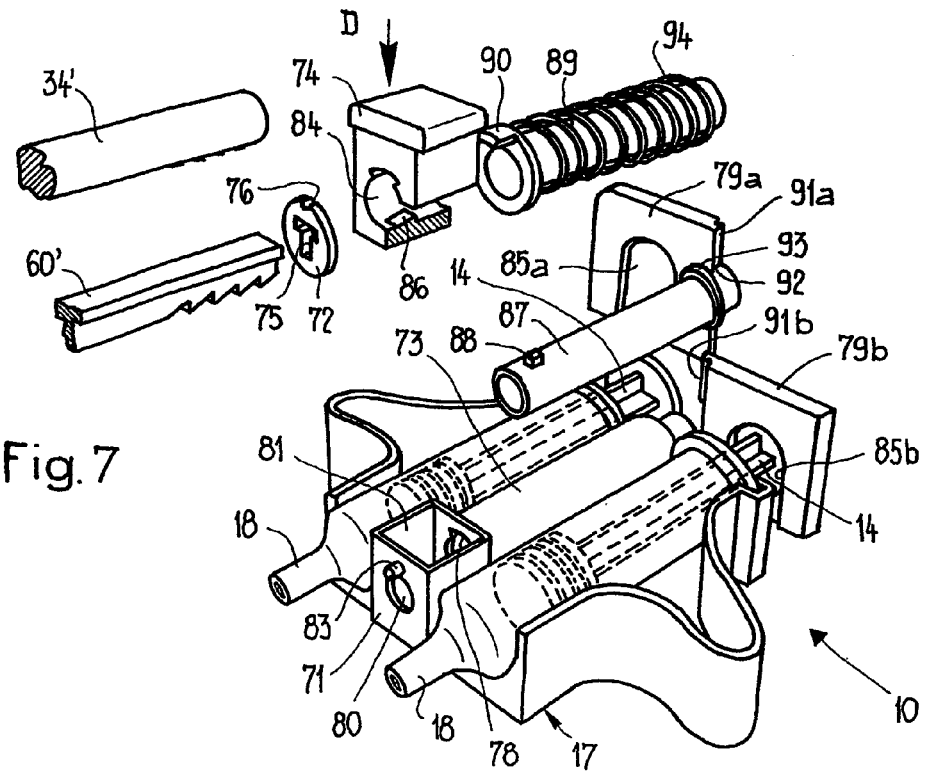
FIG. 7 is an exploded view of the connecting mechanism of a first syringe arrangement of an alternative exemplary embodiment.

FIGS. 7 to 9 show an alternative embodiment of a connecting arrangement. The connecting arrangement according to FIGS. 7 to 9 has a similar function to the arrangement according to FIGS. 4 to 6 with a slightly different design.

FIG. 7 shows an exploded view of a first syringe arrangement 10 according to this embodiment. Similarly to the preceding exemplary embodiments, the first syringe arrangement 10 is composed of a holder 17 in which two syringes 18 are arranged. The holder 17 is provided with a mounting element 71. The mounting element 71 is used to receive a coding disc 72 and an unlocking knob 74. For this purpose, the mounting element 71 is provided with a longitudinal opening 81 for receiving the unlocking knob 74. An opening 80 is used to receive the coding disc 72 and to receive extension projections 60' or 34' of a second syringe arrangement or of a mixer. A pin 83, which fits into a groove 76 in the coding disc 72, is provided on the mounting element 71. As a result, the position of the coding disc 72 can be defined precisely. The coding disc 72 has an opening 75 with T-shaped cross section. The connecting projection 60' also has a T-shaped cross section so that the second syringe arrangement 20, which is connected to a T-shaped connecting projection 60', can be connected to the first syringe arrangement 10 only in a precisely defined position.

A cylindrical guide 73 is arranged in the holder 17 adjacent to the mounting element 71. The cylindrical guide 73 is used to hold a locking tube 89. The locking tube 89 has a projection 90. The unlocking knob 74 is held in the longitudinal opening 81 so as to be displaceable in the direction of the arrow D (see FIG. 8b). The unlocking knob 74 has itself an opening 84 for receiving the connecting projection 60'. A latching cam 86 in the opening 84 of the unlocking knob 74 is used to connect in a latching fashion to saw teeth 62' of the connecting projection 60'.

Figure 8A:
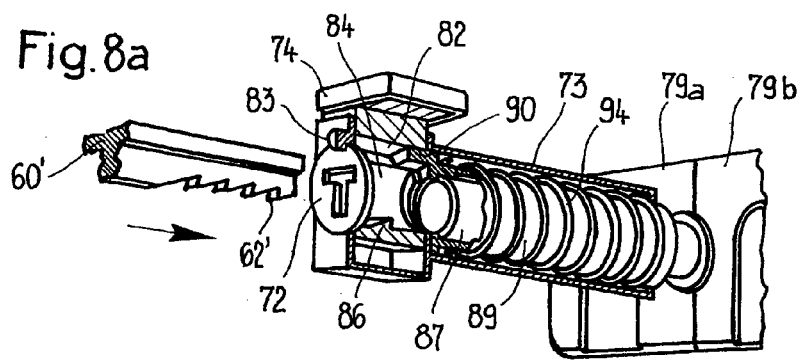
FIGS. 8a, 8b are detailed illustrations of the locking and unlocking mechanism of the connecting arrangement according to FIG. 7, FIGS. 9a to 9d are schematic illustrations of the mixing process of the exemplary embodiment according to FIG. 7 in a perspective illustration.
Figure 8B:
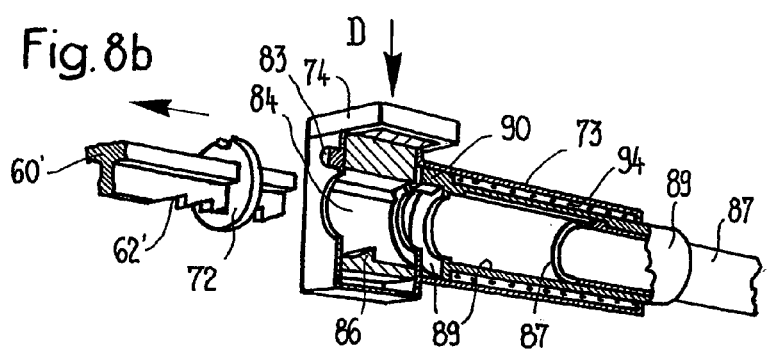

If the locking tube 89 is in the position shown in FIG. 8a, the projection 90 engages under the upper boundary face 82 of the opening 84 of the unlocking knob 74. The unlocking knob can therefore not be pressed in the direction of the arrow D (see FIG. 8b). For this reason, the connecting projection 60', which is inserted into the opening 84, cannot be removed in the position shown in FIG. 8a. The opening 84 is also constructed in such a way that a connecting projection 34' can be received in a positively locking fashion. The connecting projection 34' also has saw teeth which engage with the latching cam 86.

An activation element 87 (see also FIG. 8b) is arranged within the locking tube 89. The activation element 87 can be connected by means of clips 79a, 79b. The clips 79a, 79b can be displaced perpendicularly with respect to the displacement direction of the plungers 14 so that they can be connected to one another in the manner of a tongue and groove. The clips 79a, 79b can be pushed with their longitudinal recess 85a, 85b over the ends of the plungers 14 in this case. The clips 79a, 79b are provided with an opening 92 on the sides 91a, 91b facing one another. The opening 92 is used to receive a latching projection 93 on the activation element 87 in a latching fashion.

In the assembled state, the activation element 87 is arranged in the locking tube 89. The locking tube 89 itself is held in the cylindrical guide 73 so as to be displaceable in the axial direction. The locking tube 89 is biased by means of a spring 94. A cam 88, which is guided in a groove (not illustrated) of the locking tube 89 is provided on the activation element 87. This ensures, on the one hand, that, in order to remove the connecting projection 60', the projection 90 can be removed, counter to the spring force of the spring 94, from a centring opening 78 which is present in the mounting element 71, and that the upper boundary face 82 of the opening 84 of the unlocking knob 94 is thus cleared. On the other hand, the locking tube 89, and thus the projection 90, can be aligned with the centring opening 78 owing to the groove-cam combination with the activation element 87. The unlocking knob 74 can be blocked by the projection 90 only if the projection 90 can be guided through the centring opening 78.

The first and second syringe arrangements 10, 20 are then connected to one another in such a way that the connecting projection 60' moves through the coding disc 72 into the opening 84 of the unlocking knob 74 and that the saw teeth 62' latch with the restraining cam 86 (see FIG. 9a). The components are then mixed by activating the plungers of the syringes 18 of the first syringe arrangement 10 (see FIG. 9b). As soon as the ends of the plungers are at the same level, the two clips 79a, 79b can be fitted onto the plungers 14 and connected to one another (see FIG. 9a).

Figure 9C:
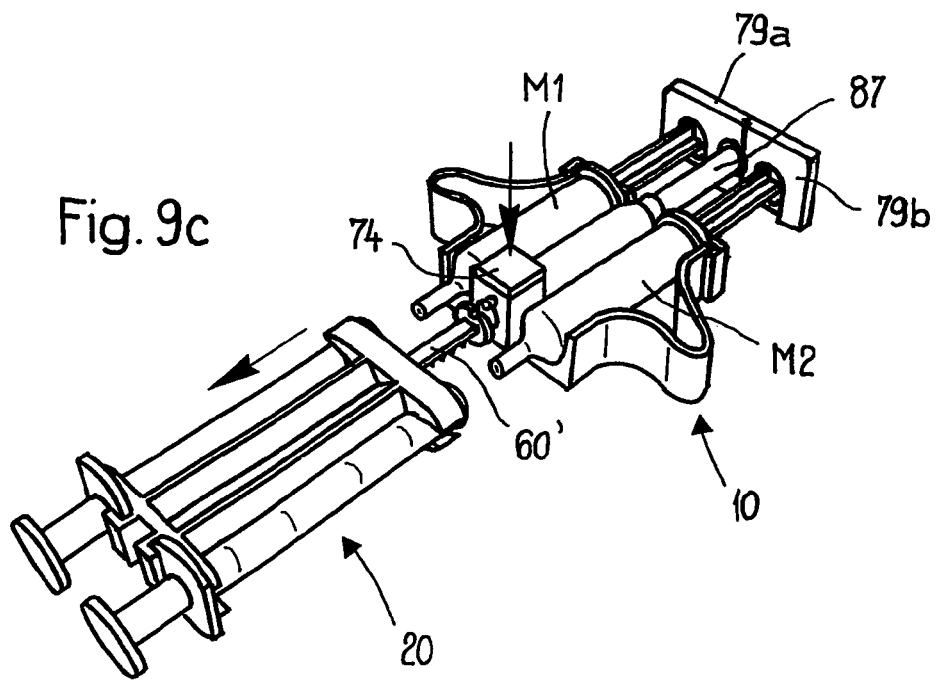

In the situation shown in FIG. 9b (see also FIG. 8a), the projection 90 of the locking tube 89 is located under the upper boundary face 82 of the opening 84 of the unlocking knob 74. As a result, the connection cannot be unlocked and the syringe arrangements 10, 20 cannot be separated from one another. When the plungers 14 of the syringes of the first syringe arrangement 10 are activated, the activation component 87 is connected to the clips 79a, 79b. By moving the plungers 14 backwards (see FIG. 9c), the activation element 87 is also pulled back. As a result, the locking tube 89 is also pulled back and clears the boundary face 82 of the unlocking knob 74 (see FIGS. 8a and 9c). By pressing the locking knob 74, it is possible, as shown in FIG. 9c, to remove the second syringe arrangement 20 from the first syringe arrangement 10. The coding disc 72 remains here on the connecting projection 60'.

This ensures that the syringe arrangements 10, 20 cannot be separated from one another until the mixtures M1, M2 are located in the syringes 18 of the first syringe arrangement 10 as a result of the backward and forward transfer. If the transfer were to take place only from the second syringe arrangement 20 into the first syringe arrangement 10, the locking tube 89 would not be pulled back, because originally there is no connection between the plunger 14 and the locking tube or the activation element 87. If the transfer takes place only from the first syringe arrangement 10 into the second syringe arrangement 20 and there is not a transfer back, the unlocking knob 74 cannot be activated either.

Figure 9D:
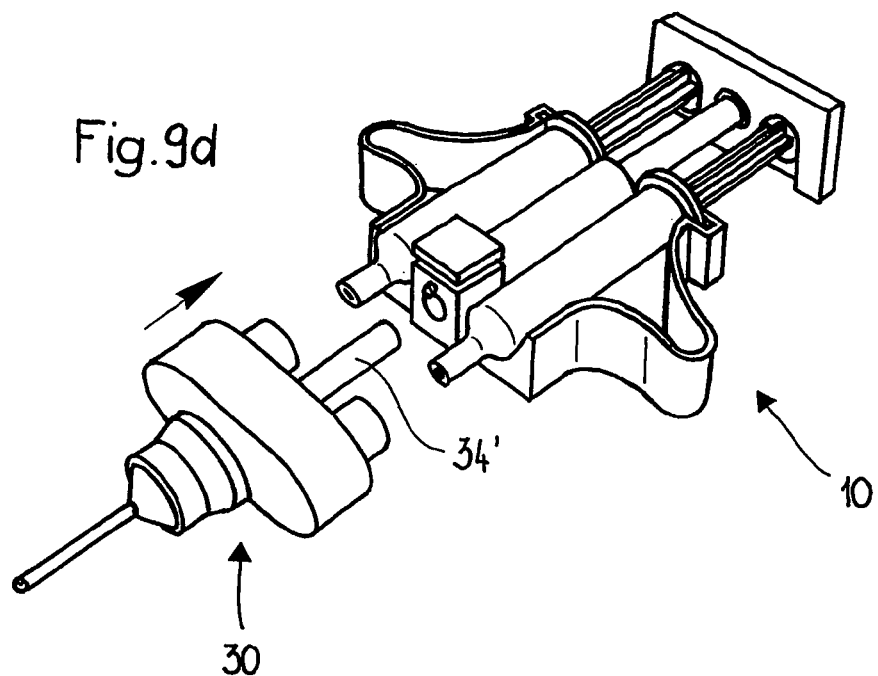
Figure 10:
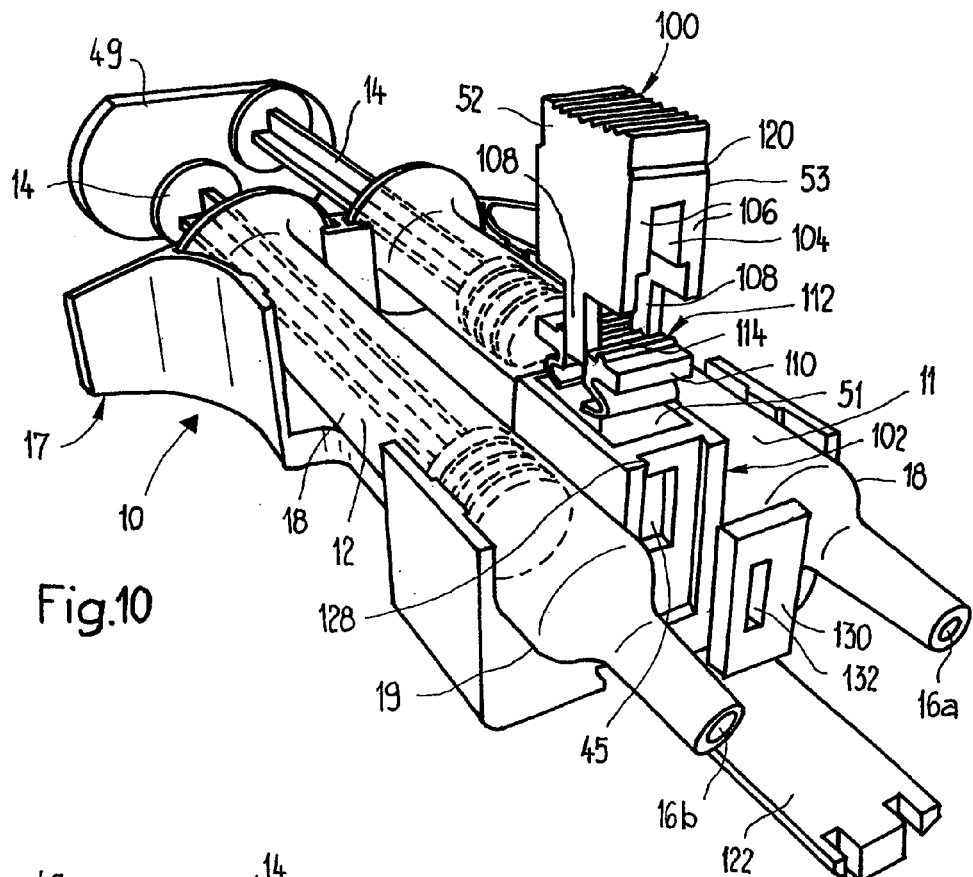
FIG. 10 is a perspective exploded illustration of a first syringe arrangement of a further embodiment.
Figure 11:
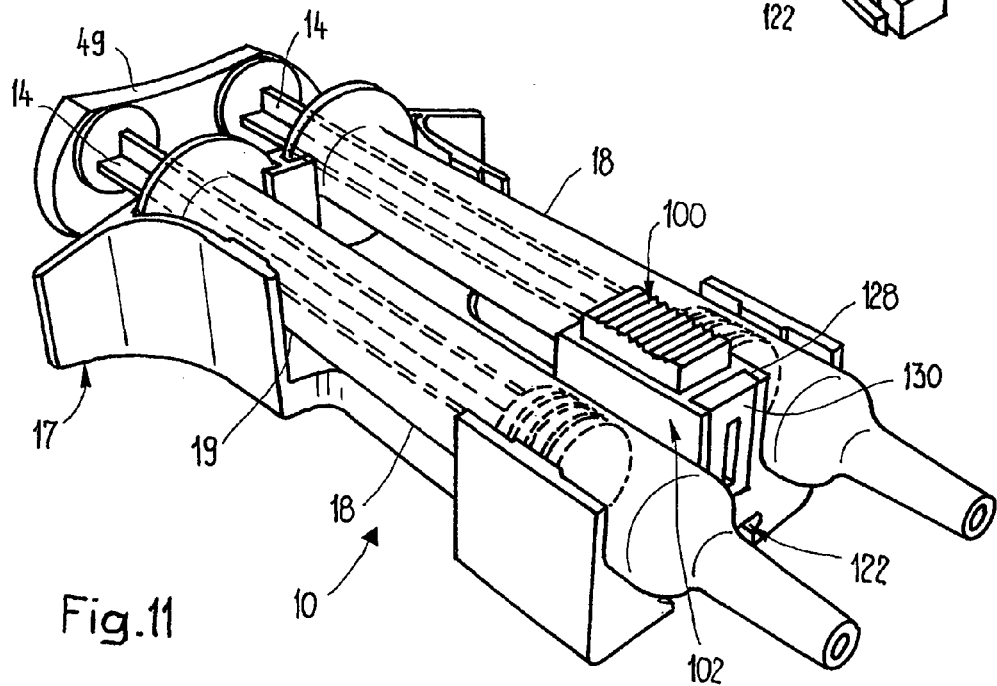
FIG. 11 is a perspective illustration of the first syringe arrangement according to FIG. 10, FIG. 12 in a longitudinal section of the first syringe arrangement according to FIGS. 10 and 11, ready for connection to a second syringe arrangement.

In the last step shown in FIG. 9d (see also FIG. 8b), a mixing device 30 is connected to the first syringe arrangement 10, similarly to how it is shown in FIG. 6d. The connecting projection 34' engages in the opening 84 of the activation knob 74. The saw teeth 37' latch with the latching cam 86 here.

The embodiment of the system according to the invention which is shown in FIGS. 10-19 differs from the two embodiments already described, in particular with respect to the design of the unlocking knob 100 and its locking in the holder 17 of the first syringe arrangement 10.

As is apparent in particular from FIGS. 10-15, the mounting element 102 for the unlocking knob 100 is located at the front end of the holder 17. The mounting element 102 has in turn a longitudinal opening 51 for receiving the unlocking knob 100. Protruding from the head part 52 of the unlocking knob 100 are sidewalls 106 which form the body part 53 and laterally delimit a depression 104 which passes through the unlocking knob 100 in the longitudinal direction and are provided with rod-like extensions 108 on the side facing away from the head part 52. A bottom element 110 which is fabricated from a rubber-elastic material and which forms the lower boundary face 112 of the depression 104 and is provided in the region of this boundary face 112 with saw-tooth-like projections 114 is supported by these extensions 108. A web-like spacer part, on which a spring part 116 of C-shaped cross section is integrally formed, protrudes on the underside from the board-like part of the bottom element 110 which has these saw-tooth-like projections 114. When the unlocking knob 100 has been inserted into the mounting element 102, the free ends of the spring part 116 are supported on the holder 17 and force the unlocking knob 100 in the direction against its upper end position, which is defined by a stop 120 on the unlocking knob 110 and a corresponding stop 120' on the mounting element 102.

On both sides of the bottom element 110 the projections 108 protrude in the downward direction over the spring part 116 and are intended to interact with a locking slide 122. This locking slide 122 is mounted on the holder 17 so as to be displaceable in the longitudinal direction of the first syringe arrangement 10, and has, on its underside, a groove 124 which runs in the longitudinal direction and is closed off at both its ends. A driver pin 126 of the extension 57 engages in this groove 124. As in the example shown further above, the extension 57 is mounted in the holder 17 so as to be displaceable in the longitudinal direction and is firmly connected to the connecting plate 49, which is intended to displace the pistons 14 of the syringes 18—which are inserted into the syringe receptacles 19 of the holder 17—together from their extended position shown in FIGS. 12-14 into the retracted position shown in FIGS. 11 and 15.

Figure 13:
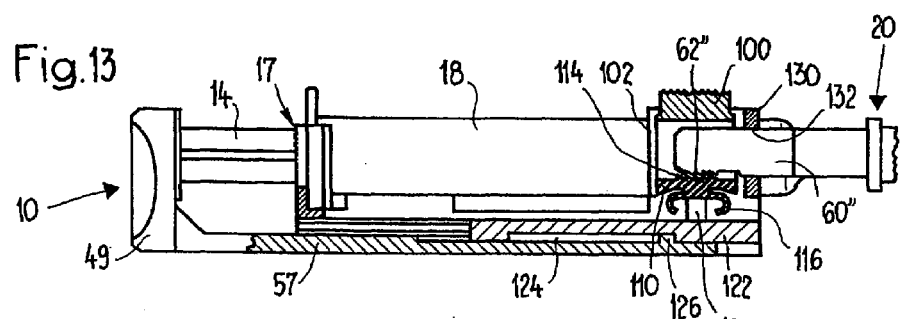
FIG. 13 shows, in the same illustration as FIG. 12, the first syringe arrangement connected to the second syringe arrangement.

In the extended position, the driver pin 126 bears against the rear end of the groove 124 and holds the locking slide 122 in a position in which the extensions 108 are cleared and the locking knob 100 can thus be moved in the direction of the arrow D. If, in order to empty the chambers 11, 12 of the syringes 18, the connecting plate 49 is displaced into the retracted position, the driver pin 126 entrains the locking slide 122 in the end region of the corresponding displacement path and displaces it underneath the extensions 108, causing the unlocking knob 100 to be held in its upper end position and preventing it from being displaced in the direction of the arrow D, as is shown by FIG. 13.

Figure 19:
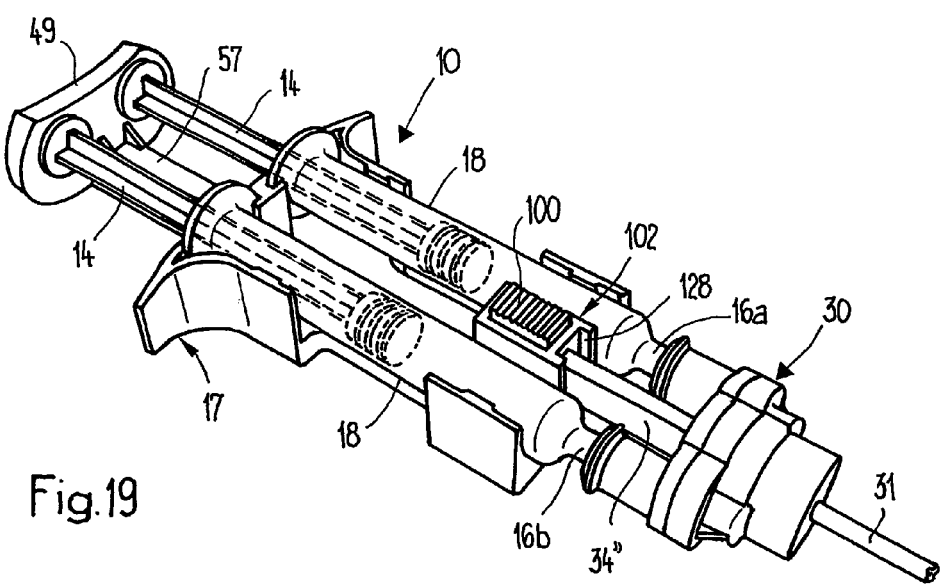

The mounting element 102 is also provided on its front side with an opening 45 whose cross section is matched to the cross section of the connecting projection 34" of the mixer 30, see also FIG. 19 in respect of this. In addition, the mounting element 102 has, on its end side, a dove-tail-like guide 128 for a small coding element 130 which can be inserted from above into the guide 128 and is held in the mounting element 102 in the mounted position by means of the latching cam (not shown) at a corresponding depression. It has already been mentioned before now that the sidewalls of the dove-tail-like guide 128 are arranged at an angle which is slightly smaller than 90° with respect to the bottom of the guide 128 so that the small coding element 130 which is composed of plastic and thus has a certain degree of elasticity, can be removed from the guide 128 by means of a force of a specific magnitude which extends in the axial direction.

Figure 16:
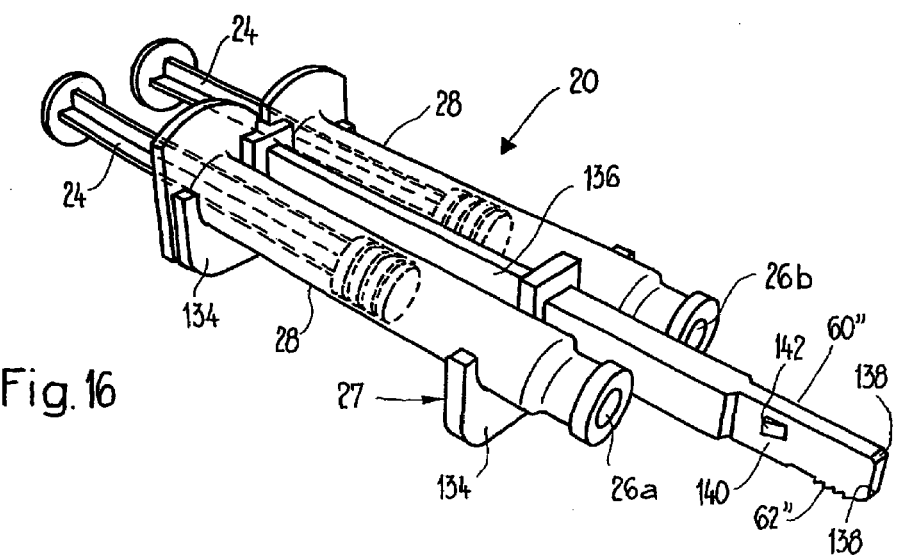
FIG. 16 is a perspective illustration of the second syringe arrangement of the further embodiment.
Figure 17:
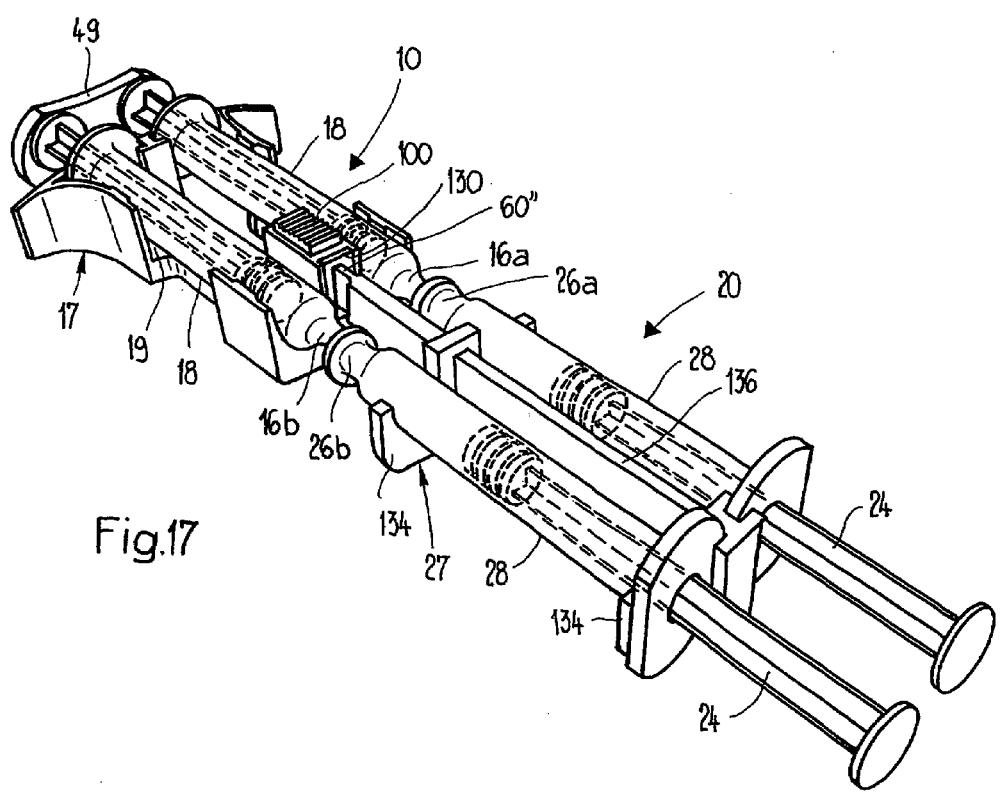
FIG. 17 is a likewise perspective illustration of the first syringe arrangement connected to the second syringe arrangement.
Figure 18:
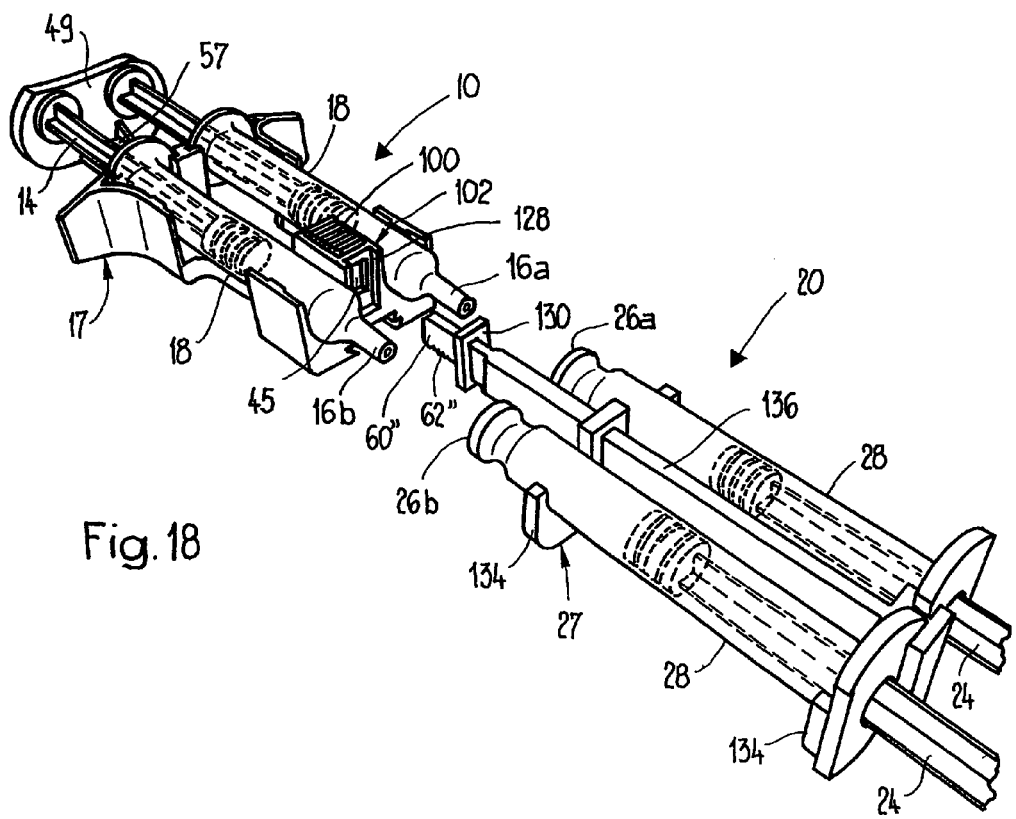
FIG. 18 is a perspective illustration of the first and second syringe arrangements which are disconnected from one another.

An opening 132 in the small coding element 130 is matched to the cross section of the connecting projection 60" of the second syringe arrangement 20, as can also be seen in particular in FIGS. 16-18. This cross section is smaller than the cross section of the connecting projection 34" of the mixing device 30.

Figure 14:
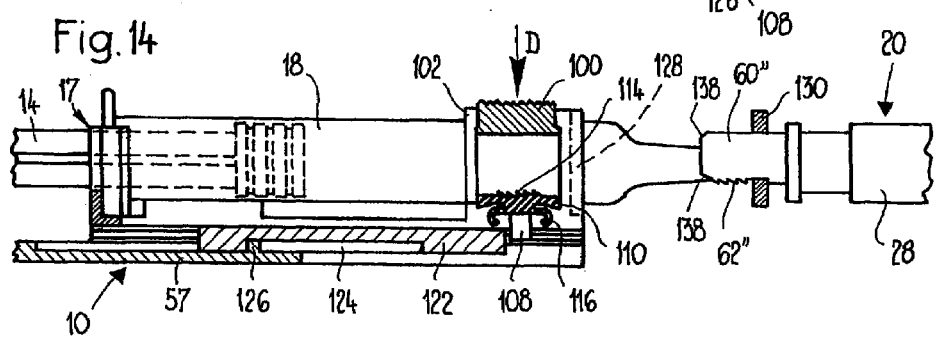
FIG. 14 shows, in the same illustration as FIGS. 12 and 13, the first syringe arrangement when the second syringe arrangement is disconnected.

The second syringe arrangement 10 has a holder 27 with two transverse walls 134 which are spaced apart from one another in the longitudinal direction, form syringe receptacles and are connected to one another centrally by means of a connecting web 136. At its rear end, the connecting web 136 has slit-like recesses on both sides for receiving protruding flanges of the syringes 28, in order to hold them in the longitudinal direction. The connecting web 136 is extended forwards through the connecting projection 60". The latter has saw teeth 62" on its underside and a chamfer 138 in its front upper and lower end regions. In addition, the two side walls 140 of the connecting projection 60" are provided with wedge-like projections which are intended to deform the small coding element 130 elastically as the connecting projection 60" is pushed in through the opening 132 of the small coding element 130 into the opening 45 and the depression 104 of the unlocking knob 100, and then to engage behind in order, as indicated in FIGS. 14 and 18, to entrain the small coding element 130 and remove it from the guide 128 as the second syringe arrangement 20 is removed from the first syringe arrangement 10.

FIG. 17 shows the first and second syringe arrangements 10, 20 which are coupled to one another. The plungers 14 of the syringes 18 of the first syringe arrangement 10 are located in their retracted position, and the plungers 24 of the syringes 28 of the second syringe arrangement 20 are correspondingly in their extended position. The unlocking knob 100 is locked.

FIG. 18 shows the two syringe arrangements 10, 20 after their separation, the small coding element 130 being seated on the connecting projection 60".

FIG. 19 shows in turn the first syringe arrangement 10 into which the mixing device 30 is now fitted.

Figure 12:
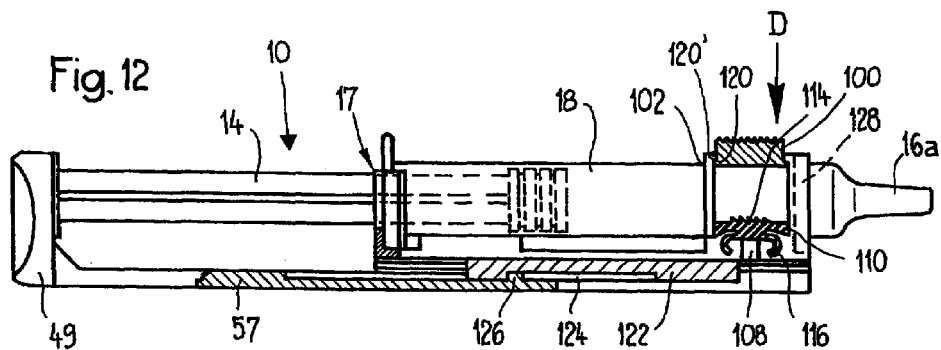

The method of operation of the embodiment shown in FIGS. 10-19 is as follows. Two syringes 18 with the components K1 and K2 are inserted into the syringe receptacles 19 of the first syringe arrangement 10. For this purpose, the extension 57 and, correspondingly, the connecting plate 49 are in the extended position; FIG. 12. Correspondingly, syringes 28 with the components K3 and K4 are inserted into the syringe receptacles of the second syringe arrangement 20; FIG. 16. The second syringe arrangement 20 is then fitted onto the first syringe arrangement 10 by pushing the connecting projection 60" through the opening 32 of the small coding element 130 and into the unlocking knob 100; FIGS. 13 and 17. For this purpose, the unlocking knob 100 can be pressed with a finger in the direction of the arrow D. However, this is not absolutely necessary, since the connecting projection 60" is able, with the lower chamfer 138 and the saw teeth 62', to displace the unlocking knob 100 counter to the effect of the spring part 116 during the insertion in the direction of the arrow D. During this fitting operation, the discharge openings 26a, 26b of the syringes 28 of the second syringe arrangement 20 are joined in the axial direction to the discharge openings 16a, 16b of the syringes 18 of the first syringe arrangement 10. The saw-tooth-like projections 114 engage with the saw teeth 62", and thus hold the second syringe arrangement 20 firmly against the first syringe arrangement 10 when the unlocking knob 100 is released or automatically; FIG. 13.

By displacing the connecting plate 49, the plungers 14 are pushed completely into the syringes 18, as a result of which the components K1 and K1 are moved into the chambers 21, 22 with the components K3 and K4 and mixed with them. Towards the end of the movement of the connecting plate 49, the locking slide 122 is displaced under the extensions 108 of the unlocking knob 110 (cf. also FIG. 13), which makes it impossible for the second syringe arrangement 20 to be decoupled from the first syringe arrangement 10 since the unlocking knob 100 cannot be pressed in the direction of the arrow D. This situation is also illustrated in FIG. 17.

Figure 15:
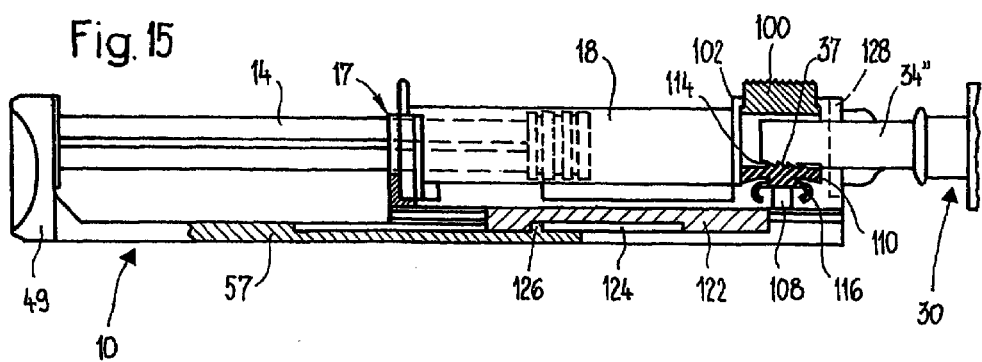
FIG. 15 shows, in the same illustration as FIGS. 12 to 13, the first syringe arrangement when a mixing device is connected.

As the next step, the plungers 24 of the syringes 28 are completely pushed in, as a result of which the mixtures M1 and M2 which are produced in them are moved back into the syringes 18 and mixed again in the process. As a result, the connecting plate 49' is moved back into its extended end position, which causes the locking slide 122 also to be displaced back out of the locking position and to clear the unlocking knob 100; FIG. 14. In order to decouple the second syringe arrangement 20, the unlocking knob 100 is then pressed, the small coding element 130 being entrained as the second syringe arrangement 20 is removed, as is shown in FIGS. 14 and 18. As a result, the path is free for the mixing device 30 to be able to be fitted onto the first syringe arrangement 10. For this purpose, a procedure is adopted which is analogous to that for the coupling of the second syringe arrangement 20 in that the connecting projection 34" of the mixing device 30 is now introduced into the depression of the head part 52 through the opening 45 and the toothing 62' meshes with the saw-tooth-like projections 114 of the unlocking knob 100; FIGS. 15 and 19. As a result of the connecting plate 49 being pushed forward, the mixtures M1 and M2 are now mixed in the mixing device 30 in order to be discharged.

For the mixing device 30 to be decoupled as necessary, the connecting plate 39 has to be pulled back into its end position, as a result of which the unlocking knob 100 is cleared.

The invention claimed is:

1. System for mixing at least four components, the system comprising a first syringe arrangement and a second syringe arrangement, the first and the second syringe arrangements each containing at least two chambers for holding each one of the components, the first syringe arrangement having a connecting means for connecting the chambers of the first syringe arrangement in a detachable fashion to the chambers of the second syringe arrangement so that components which are contained in the chambers of the second syringe arrangement can be mixed with the components which are contained in the connected chambers of the first syringe arrangement by transferring said components into the connected chambers of the first syringe arrangement to form a mixture of two components in each chamber of the first syringe arrangement, wherein at least a portion of the connecting means is removable from the first syringe arrangement upon separating said first and second syringe arrangements after said mixing, so that a mixing device for further mixing by discharging of the mixtures from the chambers of the first syringe arrangement can only be connected to said first syringe arrangement after said mixing of the components and when the second syringe arrangement and the connecting means portion have been disconnected from the first syringe arrangement.

2. System according to claim 1, wherein the connecting means includes a coding sleeve, a coding disc or a coding element.

3. System according to claim 1, wherein the connecting means includes means for connecting the chambers of the one syringe arrangement to the chambers of the other syringe arrangement in a uniquely defined fashion.

4. System for mixing at least four components, the system comprising a first syringe arrangement and a second syringe arrangement, the first and the second syringe arrangements each containing at least two chambers for holding each one of the components, wherein the syringe arrangements have means for connecting to one another in a detachable and uniquely defined fashion so that each chamber of one of the syringe arrangements can only be connected to a predetermined chamber of the other syringe arrangement so that components which are contained in the chambers of one of the syringe arrangements can be mixed with the components which are contained in the connected chambers of the other syringe arrangement by transferring said components into the connected chambers of the other syringe arrangement.

5. System according to claim 4, wherein the system has a mixing device which can be connected to the chambers of one of the syringe arrangements so that the mixed components which are contained in the chambers can be mixed further with one another by being discharged from the chambers through the mixing device.

6. System according to claim 4, wherein the connecting means for connecting one syringe arrangement to the other syringe arrangement in a uniquely defined fashion comprises a cam, a recess, a coding sleeve, a coding disc, a coding element, and/or a connecting projection.

7. System according to claim 1 or 4, wherein at least one syringe arrangement has syringes with syringe plungers which can be connected to one another.

* * * * *

UNITED STATES PATENT AND TRADEMARK OFFICE
CERTIFICATE OF CORRECTION

PATENT NO. : 7,322,956 B2 Page 1 of 1
APPLICATION NO. : 10/890149
DATED : January 29, 2008
INVENTOR(S) : Fehr et al.

It is certified that error appears in the above-identified patent and that said Letters Patent is hereby corrected as shown below:

On Title Page
item (73), the Assignee should read:

Straumann Holding AG, Basel (CH)

Signed and Sealed this

Sixth Day of May, 2008

JON W. DUDAS
*Director of the United States Patent and Trademark Office*